United States Patent
Takino et al.

(10) Patent No.: US 7,765,614 B2
(45) Date of Patent: Aug. 3, 2010

(54) DISPOSABLE WEARING ARTICLE

(75) Inventors: Shunsuke Takino, Kagawa-ken (JP); Takayuki Miyoshi, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 415 days.

(21) Appl. No.: 11/466,469

(22) Filed: Aug. 23, 2006

(65) Prior Publication Data

US 2007/0083177 A1      Apr. 12, 2007

(30) Foreign Application Priority Data

Oct. 12, 2005      (JP)      ............... 2005-298117

(51) Int. Cl.
  *A41B 13/08*      (2006.01)
  *A61F 13/15*      (2006.01)
  *A61F 13/20*      (2006.01)

(52) U.S. Cl. .................................... 2/111; 604/385.11

(58) Field of Classification Search ............... D24/124, D24/126; 604/385.01, 385.04, 385.05, 385.11, 604/385.28, 385.29, 385.3, 389, 390, 391; 24/442, 306; 2/69, 400, 402, 219, 220, 221, 2/111

See application file for complete search history.

(56) References Cited

U.S. PATENT DOCUMENTS

| | | | |
|---|---|---|---|
| 5,163,932 A | | 11/1992 | Nomura et al. |
| 5,516,567 A | * | 5/1996 | Roessler et al. ............. 428/40.1 |
| 5,605,735 A | * | 2/1997 | Zehner et al. ................ 428/100 |
| 6,213,991 B1 | * | 4/2001 | Kling et al. ............. 604/385.01 |
| 6,302,871 B1 | | 10/2001 | Nakao et al. |
| 6,443,940 B1 | | 9/2002 | Ashton et al. |
| 6,503,235 B2 | * | 1/2003 | Suzuki et al. ............. 604/385.11 |
| 6,726,669 B2 | * | 4/2004 | Shimada et al. .......... 604/385.29 |
| 7,198,622 B2 | * | 4/2007 | Dahlgren ...................... 604/386 |
| 7,288,079 B2 | * | 10/2007 | Toyoshima et al. ..... 604/385.01 |
| 2003/0158535 A1 | * | 8/2003 | Dahlgren ...................... 604/391 |
| 2005/0131378 A1 | * | 6/2005 | Sasaki et al. ................ 604/387 |

FOREIGN PATENT DOCUMENTS

| | | |
|---|---|---|
| JP | 5119930 | 2/1976 |
| JP | 2000-504975 | 4/2000 |
| JP | 2606778 | 10/2000 |
| JP | 2607820 | 6/2002 |
| JP | 2004305598 | 11/2004 |

OTHER PUBLICATIONS

EP Search Report for EP 06810077 dated Nov. 24, 2009.

* cited by examiner

*Primary Examiner*—Gary L Welch
*Assistant Examiner*—Amber R Anderson
(74) *Attorney, Agent, or Firm*—Lowe, Hauptman Ham & Berner, LLP

(57) ABSTRACT

A disposable wearing diaper includes a front panel section and a rear panel section facing each other so as to define respective waist regions. The rear panel section overlaps the outer side of the front panel section and these front and rear panel sections are connected to each other along transversely opposite side edges of the respective panel sections. The disposable diaper has finger-grips provided at positions on an upper end of the rear panel section at which the rear panel section overlap the front panel section. The finger-grip comprises a proximal zone and a distal zone extending from the proximal zone which is contiguous to the rear panel section and the distal zone is placed aside with respect to the proximal zone toward a lower end of the rear panel section.

20 Claims, 6 Drawing Sheets

DISPOSABLE WEARING ARTICLE

BACKGROUND OF THE INVENTION

The present invention relates generally to a disposable wearing article.

Japanese Utility Model Registration No. 2606778 (REFERENCE 1) and Japanese Utility Model Registration No. 2607820 (REFERENCE 2) respectively disclose disposable pants-type diapers each improved to facilitate the front and rear waist regions previously connected with each other along the transversely opposite side edges of the respective waist regions to be peeled off. These known disposable pants-type diapers include finger-grips extending outward from respective upper ends of the transversely opposite side edges so that the front and rear waist regions may be peeled off from each other by holding the finger-grips with the fingers of the wearer. National Publication of Patent Application Based On Translated Version No. 2000-504975 (REFERENCE 3) discloses disposable pants-type diaper wherein the side panels placed upon each other may be peeled off from each other to develop the diaper. In this disposable pants-type diaper, the outer side panel is provided with the finger-grips extending outward from the transversely opposite side edges.

However, with these known disposable pants-type diapers, there is an anxiety that the finger-grips may come in contact with the wearer's skin and consequentially it may create a feeling of discomfort against the wearer, since the finger-grips extending outward from the transversely opposite side edges of the panels defining the waist regions. In addition, the finger-grips held with the fingers of the wearer must be pulled downward in order to peel the panels off from each other. However, it is not necessarily easy to pull these finger-grips downward since these finger-grips are provided so as to extend upward or laterally in these known disposable pants-type diapers.

SUMMARY OF THE INVENTION

It is an object of the present invention to provide an disposable wearing article improved so that the front and rear waist regions can be easily peeled off from each other without any likelihood that the wearer might experience any feeling of discomfort.

A disposable wearing article according to the present invention comprises a first panel section and a second panel section facing each other so as to define respective waist regions, each having a longitudinal direction, a transverse direction, an inner surface and an outer surface, wherein the second panel section overlaps an outer side of the first panel section and these first and second panel sections are connected to each other along transversely opposite side edges of the respective panel sections. The second panel section is provided at positions on an upper end thereof at which the second panel section overlaps the first panel section with finger-grips, respectively. The wearing article further comprises the finger-grip comprising a proximal zone and a distal zone extending from the proximal zone which is contiguous to the second panel section and the distal zone is placed aside with respect to the proximal zone toward a lower end of the second panel section. Each finger-grip of such a configuration can be easily held with the fingers of the wearer and there is substantially no possibility that the finger-grip might come in contact with the wearer's skin.

Description as used herein "the finger-grip is continuous to the second panel section" refers to the case in which the finger-grip has been formed from a material prepared separately of the second panel section and then bonded to the second panel section and also to the case in which the finger-grip is formed integrally with the second panel section. In any case, the finger-grip is preferably made of a flexible sheet material. While a shape of the finger-grip is not specified, the distal zone is preferably tapered so that the finger-grip can be easily held by the fingers of the wearer.

More preferably, the finger-grip further comprises one side edge lying in a vicinity of the associated side edge of the second panel section and the other side edge transversely opposite to the one side edge and the finger-grip is bonded to the second panel section along the other side edge of the distal zone. The finger-grip is bonded to the second panel section not only in the proximal zone but also along the above-mentioned other side edge of the distal zone in this manner and thereby it is ensured to eliminate or to minimize the possibility that the distal zone of the finger-grip might be curled up and the finger-grip might discomfortably come in contact with the wearer's skin. In addition, such a manner of bonding facilitates the second panel section to be peeled off obliquely downward from the upper corner thereof.

The wearing article is provided with fastening means for temporary fixation of the finger-grips to the second panel section preferably provided between the distal zones of the respective finger-grips and the second panel section from the viewpoint that the finger-grips can be reliably fixed thereby so as to extend downward. Examples of the preferred fastening means include detachable fastening means adapted to be repetitively used, such as the female and male members constituting the mechanical fastener or a combination of a layer formed by a pressure-sensitive adhesive agent and a plastic film or the like serving as a landing strip on which the pressure-sensitive adhesive layer detachably sticks.

When the female and male members constituting the mechanical fastener are used as the fastening means, the female member may be permanently bonded to the finger-grip while the male member may be permanently bonded to the second panel section or vice versa. If the surface of the second panel section which faces the finger-grip has pile-like naps with which the male member of the mechanical fastener is engageable, the female member may be omitted so far as the male member is permanently bonded to the finger-grip.

When the combination of a pressure-sensitive adhesive layer and a plastic film or the like serving as the landing strip on which the pressure-sensitive adhesive layer detachably sticks is used as the fastening means, the fastening means will reliably function whether the pressure-sensitive adhesive layer or the landing strip is permanently bonded to the finger-grip.

Instead of providing the fastening means in the manner as has been described just above, a portion of the finger-grip may be temporarily bonded to the second panel section by means of heat-seal.

The present invention is applicable to the pants-type disposable wearing article as well as to the open-type disposable wearing article.

For the disposable wearing article of open-type, the mechanical fastener or the combination of a pressure-sensitive adhesive layer and a plastic film as the landing strip may be used as the connector means for detachably connecting the first panel section and the second panel section with each other so far as the connector means is of repetitively usable type.

For the disposable wearing article of pants-type, the first panel section and the second panel section are preferably connected to each other in the manner that these first and second panel sections may be easily disconnected from each other with the hands after the article has been used. Examples of the means to connect the first and second panel sections with each other in this manner include a plurality of bonding spots arranged intermittently along the transversely opposite side edges of the article and so-called perforated lines provided in the first panel section or the second panel section so that the panel section may be easily torn off in regions of the panel section other than arrays of the bonding spots.

The front side of the article may be defined either by the first panel section or by the second panel section.

The disposable wearing article according to the present invention facilitates the first panel section and the second panel section to be peeled off from each other with the finger-grips held by the hands of the wearer, on one hand, and eliminates the anxiety that the finger-grips might discomfortably come in contact with the wearer's skin, on the other hand.

Details of the disposable wearing article according to the present invention will be more fully understood from the description of a disposable diaper as one embodiment given hereunder with reference to the accompanying drawings. It should be noted here that the present invention is not limited to such a particular embodiment.

DETAILED DESCRIPTION OF THE PREFERRED EMBODIMENTS

Figure 1:
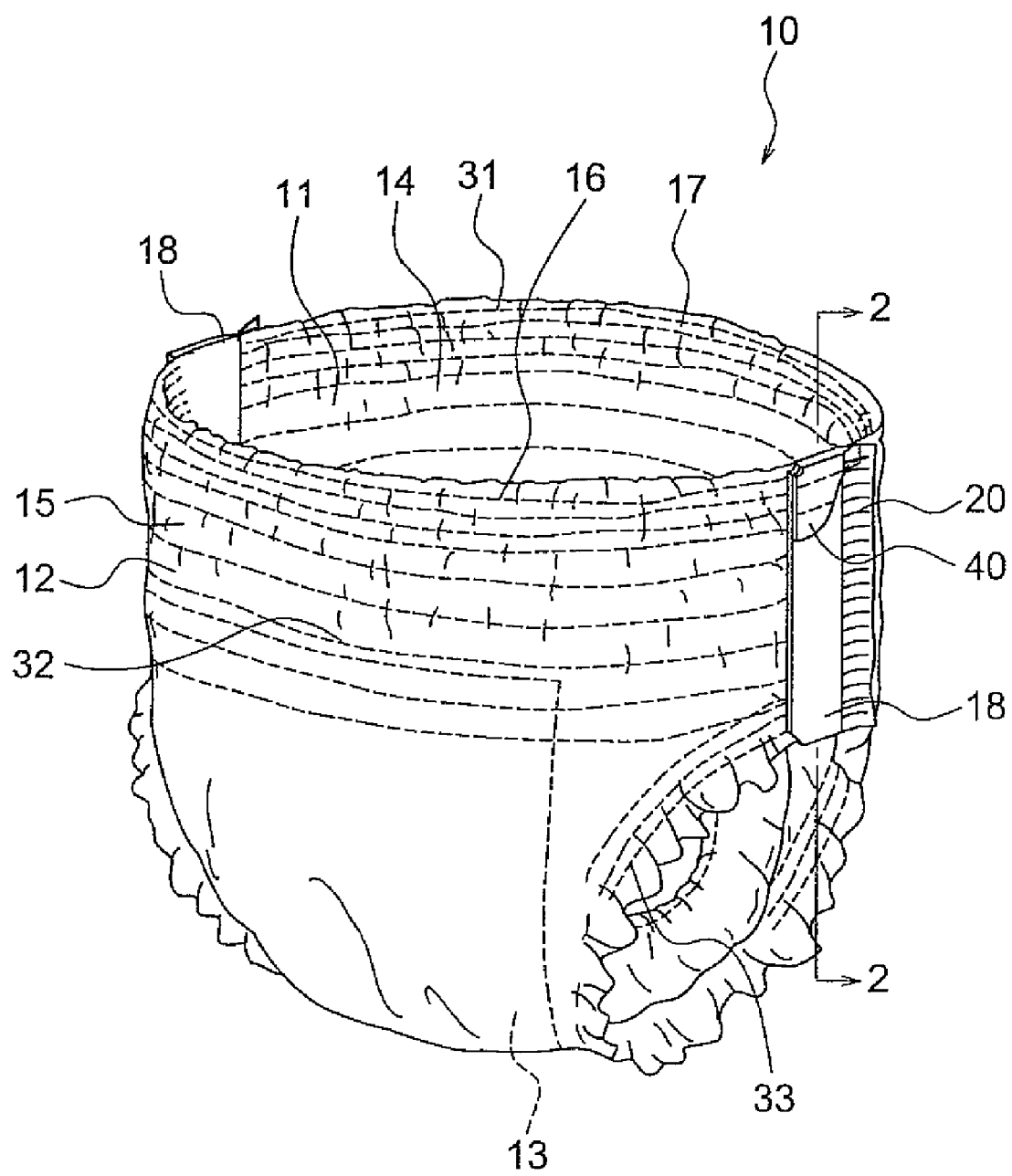
FIG. 1 is a perspective view showing a disposable diaper as one embodiment of the present invention.

A disposable diaper 10 of FIG. 1 comprises a front panel section 16 and a rear panel section 17 facing each other so as to define respective waist regions, each having a longitudinal direction, a transverse direction, an inner surface 14, an outer surface 15, and is configured basically by a liquid-pervious inner sheet 11, a liquid-impervious outer sheet 12 having pile-like naps and a body fluid absorbent core 13 sandwiched between the inner and outer sheets 11, 12. The rear panel section 17 is placed on the outer side of the front panel section 16 and connected together by the intermediary of suitable connector means along transversely opposite side edges 18 of the respective waist regions so as to form a waist-hole and a pair of leg-holes.

The rear panel section 17 is provided along the transversely opposite side edges 18 thereof with a flap 19 formed from sheet members prepared separately of the inner sheet 11 and the outer sheet 12. These sheet members forming the respective flap 19 are put flat together with the remaining regions of the inn and outer sheets 11, 12 and are bonded to the inner and outer sheets 11, 12 by means of respective bonding zones 20 defined between an upper end 21 and a lower end 22 of the rear panel section 17 along the side edges 18. The sheet member forming the flap 19 is similar to the outer sheet 12 in that the flaps 19 have liquid-impervious nature and pile-like naps.

Figure 2:
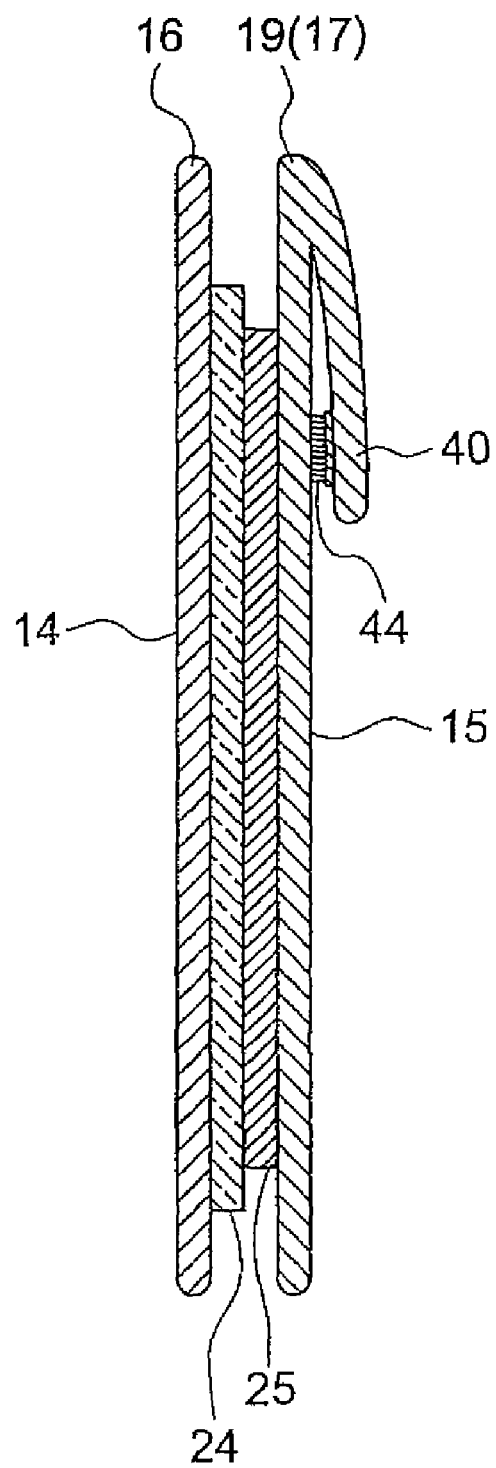
FIG. 2 is a sectional view of the disposable diaper taken along the line 2-2 in FIG. 1.

As shown in FIG. 2, the connector means adapted to connect the front and rear panel sections 16, 17 to each other comprise landing strip 24 formed by a plastic film and a pressure-sensitive adhesive layer 25 provided on the inner surface 14 of the rear panel section 17. The pressure-sensitive adhesive layer 25 is formed by a pressure-sensitive adhesive agent coated on respective base material layer provided on the inner surface 14 of the flap 19.

The front and rear panel sections 16, 17 are provided along the waist-hole and the leg-holes with waist-elastic members 31 and leg-elastic members 33, respectively. Below the waist-elastic members 31, the front and rear panel sections 16, 17 are respectively provided with auxiliary waist-elastic members 32 exhibiting a tensile stress lower than those of the waist- and leg-elastic members 31, 33 and extending in the transverse direction. The waist-elastic members 31, the auxiliary waist-elastic members 32 and the leg-elastic members 33 are sandwiched between the inner and outer sheets 11, 12 and bonded in a stretched state to at least one of these inner and outer sheets 11, 12 by known means of adhesives (not shown) such as hot melt adhesives.

The respective elastic members 31, 32, 33 are not present in a region of the front panel section 16 in which the landing strips 24 are fixed thereto and in a region of the rear panel section 17 in which the pressure-sensitive layers 25 is formed or not bonded to the sheet members defining the front and rear panel sections 16, 17 even if these elastic members 31, 32, 33 are present.

Figure 3:
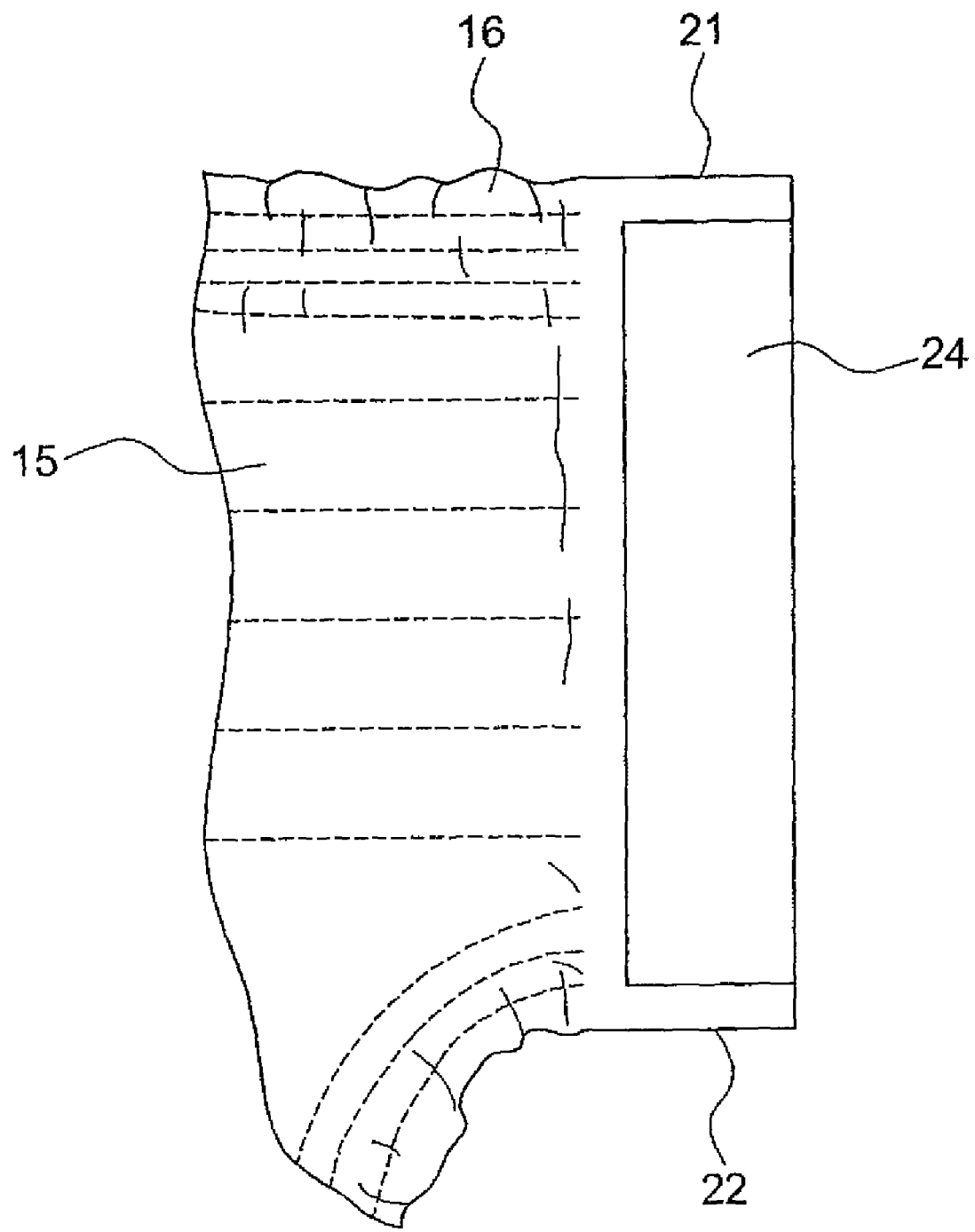
FIG. 3 is a scale-enlarged diagram illustrating a part of a front panel section in a vicinity of one of transversely opposite sides.
Figure 4:
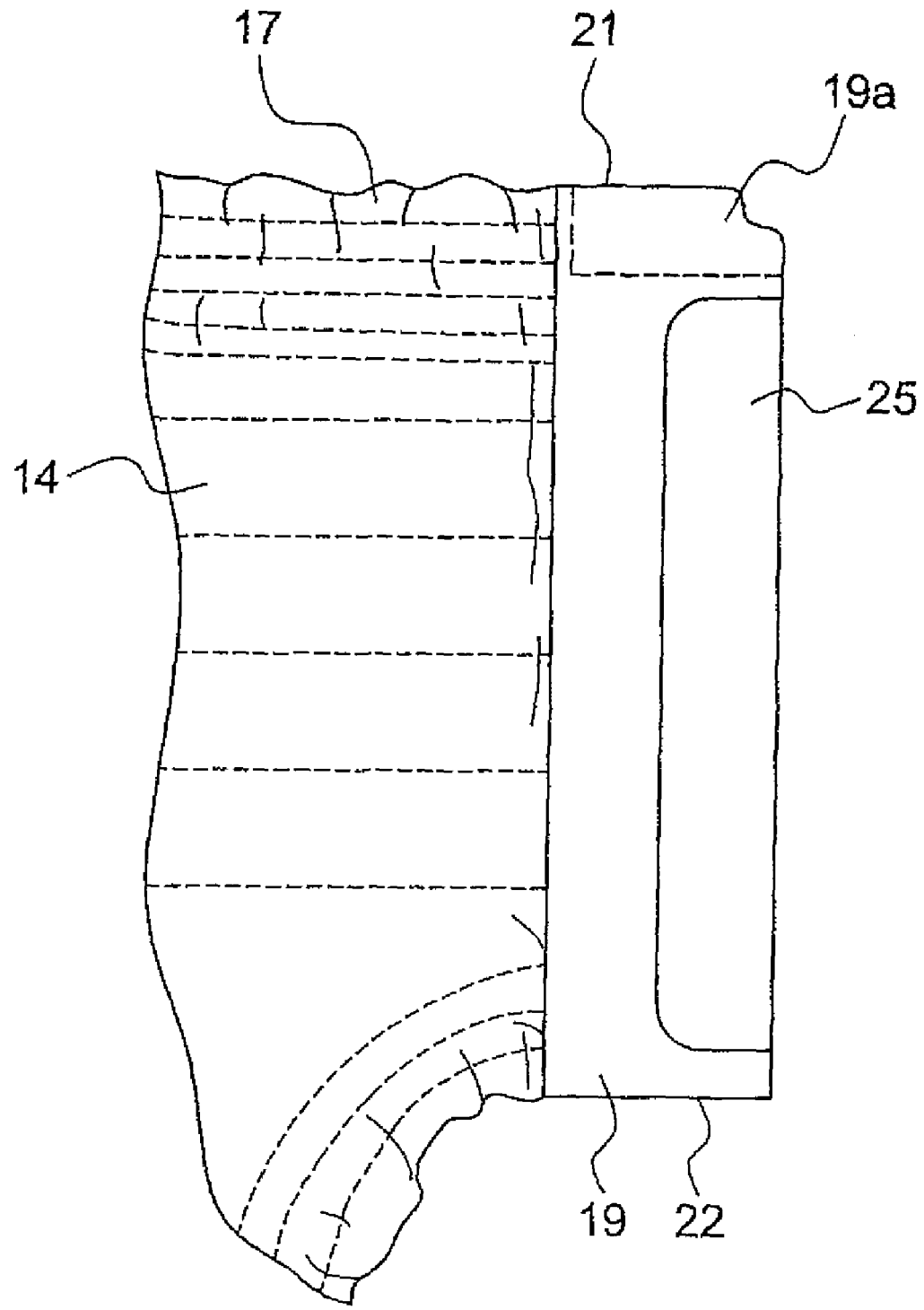
FIG. 4 is a scale-enlarged diagram illustrating a part of a rear panel section in a vicinity of one of transversely opposite sides.

As shown in FIG. 3, the landing strips 24 fixed to the outer surface 15 of the front panel section 16 in a vicinity of the transversely opposite side edges 18 of the respective waist regions preferably cover the outer surface 15 of the front panel section 16 in a manner that the upper and lower ends 21, 22 of the front panel section 16 are partially left uncovered. As shown in FIG. 4, the pressure-sensitive layers 25 formed on the inner surface 14 of the rear panel section 17 also preferably cover the inner surface 14 of the rear panel section 17 in a manner that the upper and lower ends 21, 22 of the rear panel section 17 are partially left uncovered. In other words, preferably there are dry edges free from the pressure-sensitive adhesive along the upper and lower ends 21, 22 of the rear panel section 17.

The respective upper ends of the transversely opposite side edges of the rear panel section 17 form rounded corners and portions of the rear panel section 17 including these rounded corners in a vicinity of the upper ends are differentially colored with respect to the remaining portions.

The upper end 21 of the rear panel section 17 is provided on portions thereof placed on the front panel section 16 with finger-grips 40. Each of these finger-grips 40 is formed from the sheet member of the flap 19 integrally with the rear panel section 17. The finger-grip 40 comprises a proximal zone 41 and a distal zone 42 extending from this proximal zone 41 which is contiguous to the rear panel section 17. The proximal zone 41 extends in the transverse direction on the zone along the upper end 21 of the rear panel section 17, which zone is free from the pressure-sensitive adhesive. The distal zone 42 is placed aside with respect to the proximal zone 41 toward the lower end 22 of the rear panel section 17.

The finger-grip 40 has a pair of transversely opposite side edges 43*a*, 43*b*. Of these side edges 43*a*, 43*b*, the one side edge 43*b* lying in a vicinity of the associated side edge of the rear panel section 17 extends linearly along this side edge of the rear panel section 17. The other side edge 43a opposite to the side edge 43b extends, in a vicinity of the proximal zone 41, linearly along the side edge of the flap 19 and then curves toward a tip thereof so as to get nearer to the side edge 43b.

Figure 5:
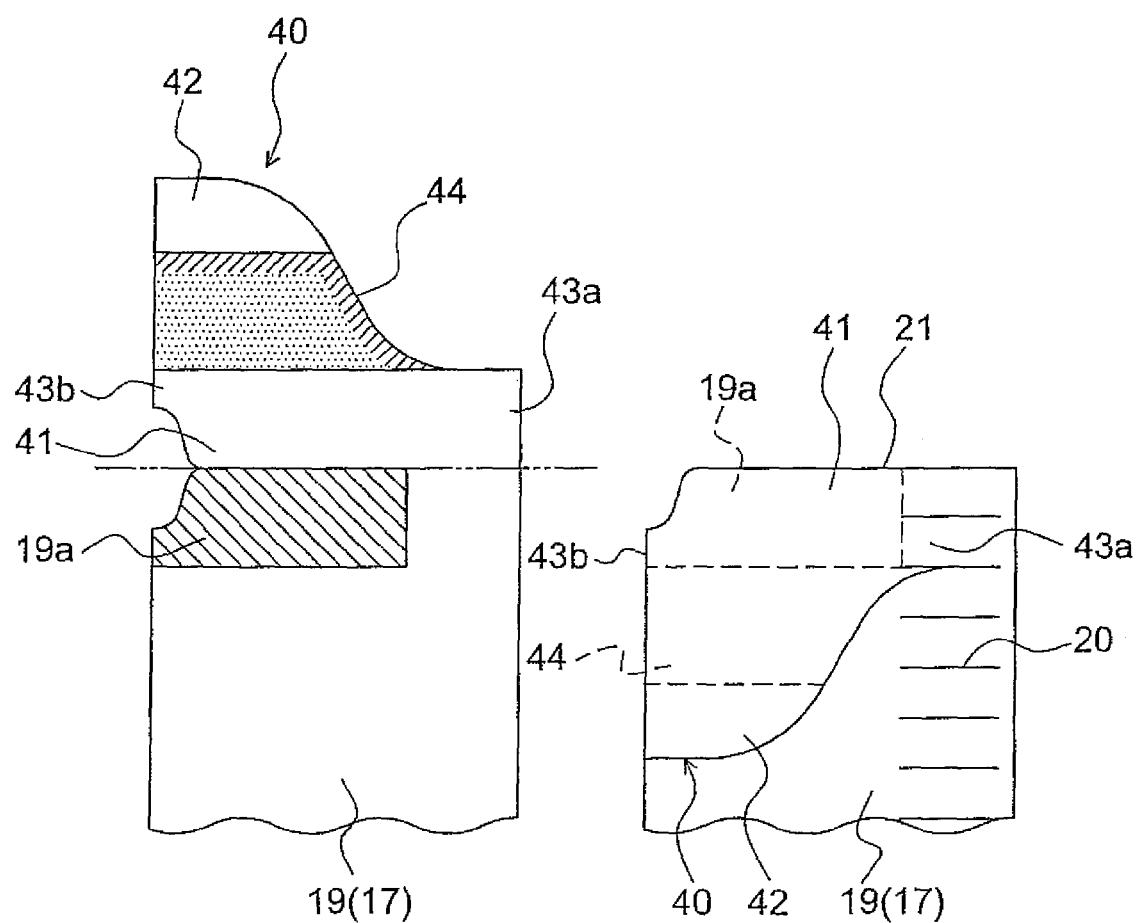
FIG. 5 is a diagram illustrating a finger-grip unfolded above an upper end of a rear panel section and this finger-grip remaining folded to face the rear panel section.

As shown in FIG. 5, the finger-grip 40 has its distal zone 42 folded back so as to face the outer surface 15 of the rear panel section 17 and the side edge 43a of the distal zone 42 is partially, i.e., only in the vicinity of the proximal zone 41, bonded to the rear panel section 17 by means of the bonding zones 20.

The distal zone 42 of the finger-grip 40 is provided on its side facing the rear panel section 17 with a male member 44 constituting the so-called mechanical fastener. The side of the flap 19 facing the finger-grip 40, i.e., the sheet member defining the outer surface 15 of the flap 19 in the rear panel section 17 has the pile-like naps adapted to come in engagement with the male member 44 of the mechanical fastener. With such an arrangement, the finger-grip 40 may be temporarily fixed to the rear panel section 17 by means of the male member 44 of the mechanical fastener.

Figure 6:
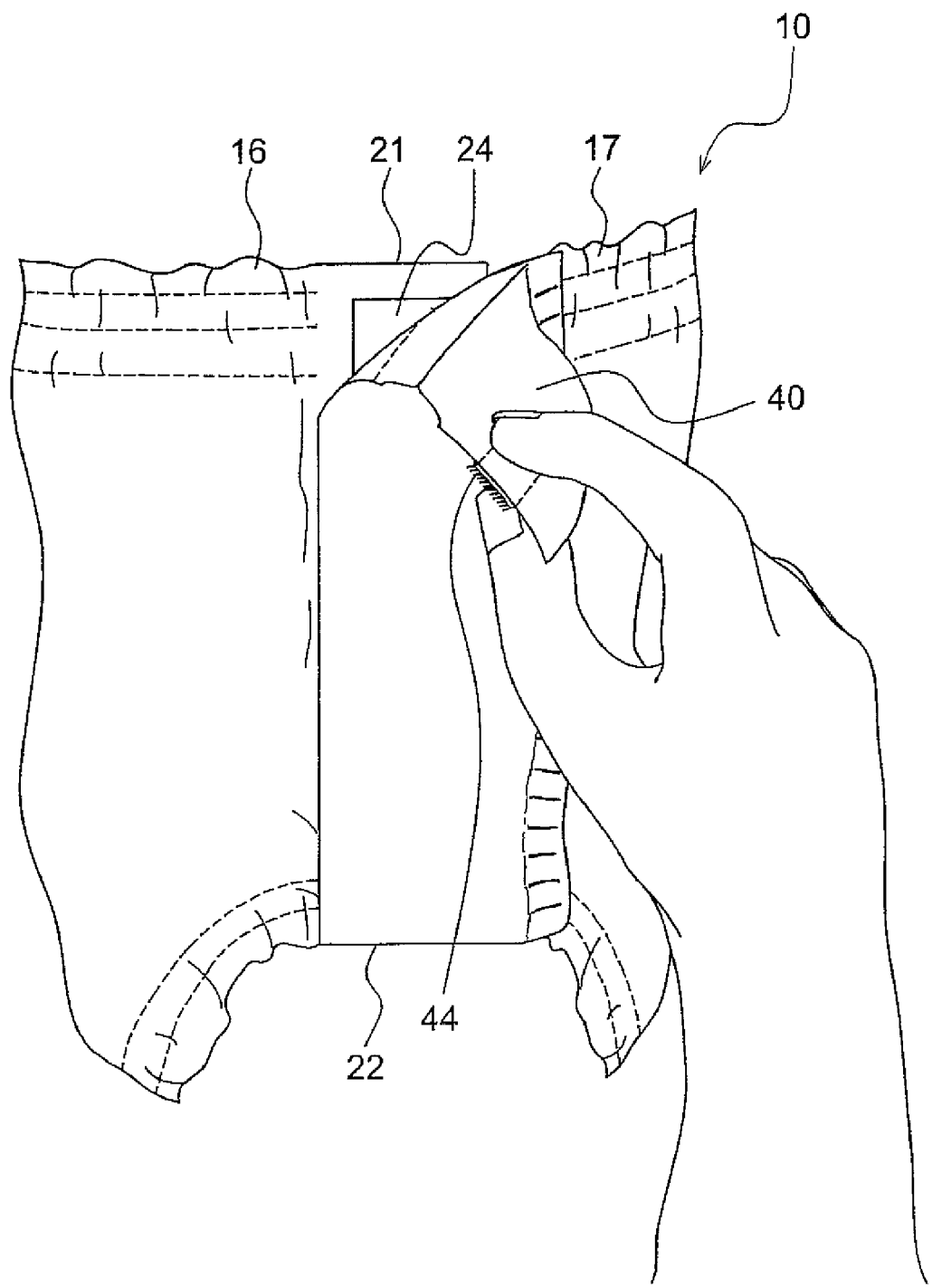
FIG. 6 is a diagram illustrating a manner in which the finger-grip gripped with the fingers and the front and rear panel sections being peeled off from each other.

As shown in FIG. 6, to peel the front and rear panel sections 16, 17 connected together by means of the above-mentioned connector means off from each other, each of the finger-grips 40 may be held with the fingers of the wearer and pulled downward. The rear panel section 17 is thereby peeled off from the upper end of the side edge 43b obliquely right- and downward from the upper left corner as viewed in FIG. 6. As has previously been described, the upper end 21 of the rear panel section 17 includes the dry edge free from the pressure-sensitive adhesive and therefore a peeling force is generated between the landing strip 24 on the front panel section 16 and the pressure-sensitive adhesive layer 25 on the rear panel section 17 as the rear panel section 17 begins to be peeled off from the upper end of the side edge 43b. The peeling force facilitates the rear panel section 17 to be peeled off from the front panel section 16. In this disposable diaper 10, the dry edge is present along the upper end 21 of the rear panel section 17 and the side edge 43a of the finger-grip 40 is bonded, partially only in the vicinity of the proximal zone 41, to the rear panel section 17. Thus, the front and rear panel sections 16, 17 can be easily peeled off from each other by pulling the finger-grip 40 obliquely downward.

In this disposable diaper 10, the front and rear panel sections 16, 17 are connected by means of the detachable connector means adapted to be repetitively used in order to check if the diaper has been soiled or not. The features that the distal zone 42 of the finger-grip 40 is placed aside, with respect to the proximal zone 41, toward the lower end 22 of the rear panel section 17 and the finger-grip 40 extends substantially downward reliably eliminate a likelihood that the finger-grip 40 might come in contact with the wearer's skin and the finger-grip 40 might create a feeling of discomfort against the wearer. The male member 44 constituting the mechanical fastener serving as the temporary fastening means interposed between the distal zone 42 of the finger-grip 40 and the front panel section 16 prevents the finger-grip 40 from being curled up. This male member 44 constituting the mechanical fastener serves to fasten the used diaper in its rolled up state for disposal. Of the upper end 21 of the rear panel section 17 the portion 19a on which the finger-strip 40 is provided is differentially colored with respect to the remaining portion so that the presence of the finger-grip 40 may be easily recognized.

Alternatively, the finger-grip 40 may be formed integrally with the rear panel section 17 by the inner and outer sheets 11, 12 of the rear panel section 17 without use of the flap 19.

It is also possible to bond the finger-grip 40 formed separately of the rear panel section 17 to the upper end 21 of the second panel section at the proximal zone 41.

The shape of the finger-grip 40 is not limited to that shown by the accompanying drawings. For example, the finger-grip 40 may be shaped to have a rectangular distal zone 42 of which the transversely opposite side edges extend in parallel to each other or to have a tapered distal zone 42 of which the transversely opposite side edges come gradually close to each other.

Alternatively, the finger-grip 40 may be bonded to the rear panel section 17 along the side edge 43a of the distal zone 42. It is also possible to bond the finger-grip 40 to the rear panel section 17 along the transversely opposite side edges 43a, 43b of the distal zone 42 so far as a portion adapted to be held with the fingers of the wearer is left. The portion adapted to be held with the fingers of the wearer has a length preferably in a range of 20 to 30 mm. As further alternative embodiment, the finger-grip 40 may be bonded to the rear panel section 17 not along a partial length but along a full length of a single side edge. The finger-grip 40 may be bonded to the rear panel section 17 continuously or intermittently along one or both side edges.

While the disposable diaper 10 illustrated herein uses only the male member of the mechanical fastener as the fastening means for temporarily fixing the finger-grip 40 to the rear panel section 17, it is possible to attach a female member of the mechanical fastener to the outer surface 15 of the rear panel section 17 with which the male member attached to the finger-grip 40 is adapted to come in engagement. In this case, the reverse arrangement is also possible, in which the female member is attached to the finger-grip 40 while the male member is attached to the rear panel section 17. It is also possible to replace the female member of the mechanical fastener by a combination of a layer of pressure-sensitive adhesive and a plastic film to be used as fastening means in the form of a landing strip. If desired, the fastening means may be left off. Specifically, the distal zone 42 of the finger-grip 40 may be partially bonded to the rear panel section 17 by suitable means such as heat-sealing, instead of temporarily fixing the finger-grip 40 to the rear panel section 17.

In the disposable diaper 10 illustrated herein, the portion 19a along the upper end 21 of the rear panel section 17 at which the finger-grip 40 is provided may have the same color as the remaining portion.

As the connector means adapted to connect the front and rear panel sections 16, 17 together, the above-described combination of the landing strip 24 and the pressure-sensitive adhesive layer 25 may be replaced by the combination of the female and male members. In this case, the male member may be attached to the front panel section 16 or the rear panel section 17. If the male member is attached to the rear panel section 17, it is possible to omit the female member in view of the fact that the outer sheet 12 defining the outer surface 15 of the front panel section 16 facing the male member has pile-like naps with which the male member is adapted to be engaged.

The front and rear panel sections 16, 17 overlapping each other along the transversely opposite side edges 18 may be bonded directly to each other without use of any connector means. In this case, the front and rear panel sections 16, 17 are preferably bonded to each other so that these two panel sections 16, 17 bonded together may be peeled off from each other with the hands of the wearer or include zones other than the respective bonded zones along which these two panel sections 16, 17 may be easily torn off from each other. To bond the front and rear panel sections 16, 17 to each other so that these bonded panel sections 16, 17 may be peeled off from each other with the hands of the wearer, for example, a plurality of bonding lines each extending in the transverse direction are arranged intermittently between the upper and lower ends 21, 22 of the panel sections. In this case, the finger-grips 40 are provided preferably in a vicinity of said bonding lines at the upper end 21 of the respective panel sections. To provide the zones along the transversely opposite side edges 18 which the front and rear panel sections 16, 17 may be easily torn off from each other, for example, these panel sections may be formed with perforated lines extending from the upper end 21 to the lower end 22 of the panel sections. In this case, the finger-grips 40 are provided preferably in a vicinity of the respective perforated lines at the upper end 21 of the respective panel sections.

In contrast with the embodiment illustrated herein, it is possible to place the font panel section 16 on the outer side of the rear panel section 17 and to provide the finger-grips 40 on the upper end 21 of the front panel section 16.

As a stock material for the inner and outer sheets 11, 12, the well known material usually used for this type of article such as a nonwoven fabric, a woven fabric or a plastic film may be optionally used.

As a stock material for the core 13, a mixture of fluff pulp and super-absorbent polymer particles wrapped with a sheet material such as a tissue paper or a nonwoven fabric exhibiting high liquid-permeability and/or high liquid-diffusivity, or fluff pulp wrapped with such sheet material may be used.

When the pressure-sensitive adhesive layer is used as the connector means adapted to connect the front and rear panel sections 16, 17 with each other, such pressure-sensitive adhesive layer preferably comprises a known base material plastic film in the art such as a drawn polypropylene film and a known pressure-sensitive adhesive agent in the art usually used for this type of article such as a rubber-based, acryl-based, epoxy-based or silicone-based adhesive agent coated on the base material to a thickness in a range of about 10 to 50 µm. As a stock material for the landing strip adapted to cooperate with the pressure-sensitive adhesive layer, a known plastic film or the like in the art may be used.

As a stock material for the finger-grip 40, a known sheet material in the art usually used for this type of article such as a nonwoven fabric, a woven fabric or a plastic film may be optionally used so far as the sheet material has a strength sufficient to endure a tensile force required to release engagement of said fastening means and thereby to peel the front and rear panel sections off from each other. In this case, the sheet material preferably has flexibility and suppleness. It is possible to form the finger-grip 40 from a plurality of sheets laminated one with another.

As the fastening means for temporarily fixing the finger-grip 40 to the rear panel section 17, the female and male members constituting the mechanical fastener or the combination of the pressure-sensitive adhesive layer in the art and the landing strip made of a known plastic film or the like facing the pressure-sensitive adhesive layer may be used.

As the elastic members 31, 32, 33, a thread rubber, a flat rubber or the like made of a known material such as a natural rubber, a synthetic rubber or a urethane foam may be used.

To bond the respective members one to another, bonding means usually used for making this type of article, for example, a suitable adhesive agent such as a hot melt adhesive, heat-sealing or sonic-sealing means may be used.

The present invention is applicable not only to the pants-type disposable diaper but also to pants-type disposable wearing article such as training pants, pants for incontinent patient or sanitary briefs.

The entire discloses of Japanese Patent Application No. 2005-298117 filed on Oct. 12, 2005 including specification, drawings and abstract are herein incorporated by reference in its entirety.

What is claimed is:

1. A disposable wearing article, comprising:
a first panel section and a second panel section facing each other so as to define respective waist regions, each having a longitudinal direction, a transverse direction, an inner surface and an outer surface, wherein said second panel section overlaps and is connected to the first panel section along transversely opposite side portions of said panel sections,
said second panel section being provided along an upper edge of the side portions, where said second panel section overlaps said first panel section, with finger-grips; and
each said finger-grip comprising a proximal zone contiguous to the upper edge of said second panel section and a distal zone contiguous to said proximal zone and folded downward toward a lower edge of said second panel section,
wherein each said finger-grip is directly releasably attachable to the second panel section.

2. The wearing article set forth by claim 1, wherein each said finger-grip further comprises a pair of transversely opposite first and second side edges,
wherein
the first side edge extends along a side edge of the second panel section;
the second side edge is shorter in length than the first side edge, and is spaced in the transverse direction from the first side edge; and
said finger-grip is bonded to said second panel section along said second side edge.

3. The wearing article set forth by claim 1, further comprising a fastening element for releasable attachment of said finger grip to said second panel section, said fastening element being provided between said finger-grip and said second panel section.

4. The wearing article set forth by claim 3, wherein said fastening element comprises a male member attached to one of said outer surface of said second panel section and the finger-grip and releasably engageable with the other of said outer surface of said second panel section and the finger-grip to prevent the finger-grip from being curled up.

5. The wearing article set forth by claim 1, wherein said first panel section and said second panel section are detachably connected to each other by means of a connector.

6. The wearing article set forth by claim 5, wherein said connector comprises a pressure-sensitive adhesive provided on the inner surface of the second panel section for releasably connecting the first panel section to the second panel section.

7. The wearing article set forth by claim 6, wherein said connector further comprises a landing strip provided on the outer surface of the first panel section and directly releasably attachable to the pressure-sensitive adhesive.

8. The wearing article set forth by claim 7, wherein said pressure-sensitive adhesive covers the landing strip while leaving the upper and lower edges of the second panel section free from the pressure-sensitive adhesive.

9. The wearing article set forth by claim 7, further comprising:
a waist-elastic member provided along a waist-hole defined by the first and second panel sections;
a leg-elastic member provided along each leg-hole defined by the first and second panel section; and an auxiliary waist-elastic member provided below the waist-elastic member in the transverse direction and having a lower tensile stress than both said waist-elastic member and said leg-elastic member.

10. The wearing article set forth by claim 9, wherein said landing strip is free from the waist-elastic member, said leg-elastic member and the auxiliary waist-elastic member.

11. The wearing article set forth by claim 6, wherein said proximal zone extends in the transverse direction along the upper edge of the second panel section and is free from the pressure-sensitive adhesive.

12. The wearing article set forth by claim 1, wherein each said finger-grip is a flap configured integrally with the second panel section.

13. The wearing article set forth by claim 1, wherein each said finger-grip is configured integrally with the second panel section by an inner sheet and an outer sheet of the second panel section.

14. The wearing article set forth by claim 1, wherein the first panel section and the second panel section are bonded together along bonding lines, each said bonding line extending in the transverse direction, said bonding lines being arranged intermittently in the longitudinal direction between the upper and lower edges of the first and second panel sections.

15. The wearing article set forth by claim 14, wherein the finger-grip is folded on the second panel section and the proximal zone is partially bonded to the second panel section by means of at least one of the bonding lines.

16. The wearing article set forth by claim 1, wherein said wearing article is configured as a pants-type disposable wearing article or an open-type disposable wearing article.

17. The wearing article set forth by claim 1, wherein the finger-grip comprises along the upper edge of the second panel section, a portion which is differentially colored with remaining portions of the wearing article.

18. The wearing article set forth by claim 1, wherein upper parts of the transversely opposite side portions of the second panel section include rounded corners colored differentially with remaining portions of the wearing article.

19. A disposable wearing article, comprising:
a first panel section and a second panel section facing each other so as to define respective waist regions, each having a longitudinal direction, a transverse direction, an inner surface and an outer surface, wherein said second panel section overlaps and is connected to the first panel section along transversely opposite side portions of said panel sections,
said second panel section being provided along an upper edge of the side portions, where said second panel section overlaps said first panel section, with finger-grips; and
each said finger-grip comprising a proximal zone contiguous to the upper edge of said second panel section and a distal zone contiguous to said proximal zone and folded downward toward a lower edge of said second panel section,
wherein each said finger-grip further comprises a pair of transversely opposite first and second side edges, wherein
the first side edge extends along a side edge of the second panel section;
the second side edge is shorter in length than the first side edge, and is spaced in the transverse direction from the first side edge, and
said finger-grip is releasably bonded to said second panel section along said second side edge.

20. The wearing article set forth by claim 19, wherein
the first panel section and the second panel section are bonded together at bonding lines arranged intermittently in the longitudinal direction between the upper and lower edges of the first and second panel sections; and
said second side edge of the finger-grip is releasably bonded to the second panel section by means of at least one of the bonding lines.

* * * * *